US012616422B2

(12) United States Patent
Nie et al.

(10) Patent No.: US 12,616,422 B2
(45) Date of Patent: May 5, 2026

(54) PREDIABETES DETECTION SYSTEM AND METHOD BASED ON COMBINATION OF ELECTROCARDIOGRAM AND ELECTROENCEPHALOGRAM INFORMATION

(71) Applicant: SHENZHEN INSTITUTES OF ADVANCED TECHNOLOGY CHINESE ACADEMY OF SCIENCES, Shenzhen (CN)

(72) Inventors: Zedong Nie, Shenzhen (CN); Jingzhen Li, Shenzhen (CN); Yuhang Liu, Shenzhen (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 1079 days.

(21) Appl. No.: 17/312,946

(22) PCT Filed: Nov. 13, 2020

(86) PCT No.: PCT/CN2020/128559
§ 371 (c)(1),
(2) Date: Jun. 11, 2021

(87) PCT Pub. No.: WO2021/238092
PCT Pub. Date: Dec. 2, 2021

(65) Prior Publication Data
US 2022/0313172 A1 Oct. 6, 2022

(30) Foreign Application Priority Data
May 29, 2020 (CN) ......................... 202010475003.6

(51) Int. Cl.
*A61B 5/00* (2006.01)
*A61B 5/33* (2021.01)
(Continued)

(52) U.S. Cl.
CPC .............. *A61B 5/7275* (2013.01); *A61B 5/33* (2021.01); *A61B 5/374* (2021.01); *A61B 5/6803* (2013.01);
(Continued)

(58) Field of Classification Search
CPC ............ A61B 2562/046; A61B 5/7275; A61B 5/7264; A61B 5/7246; A61B 5/6803;
(Continued)

(56) References Cited

U.S. PATENT DOCUMENTS

| | | | |
|---|---|---|---|
| 6,572,542 B1 * | 6/2003 | Houben ................. | G16H 50/20 |
| | | | 128/920 |
| 2008/0208072 A1 * | 8/2008 | Fadem ................... | A61B 5/291 |
| | | | 600/544 |

OTHER PUBLICATIONS

Changsheng Zhu et al., Improved logistic regression model for diabetes prediction by integrating PCA and K-means techniques, Informatics in Medicine Unlocked, vol. 17, 2019, 100179, ISSN 2352-9148, https://doi.org/10.1016/j.imu.2019.100179., viewed on Oct. 7, 2024 (Year: 2019).*

(Continued)

*Primary Examiner* — Unsu Jung
*Assistant Examiner* — James Moss
(74) *Attorney, Agent, or Firm* — Nitin Kaushik

(57) ABSTRACT

A prediabetes detection system and method based on combination of electrocardiogram and electroencephalogram information are provided. The system includes: a signal obtaining module, configured to obtain an electrocardiogram signal and an electroencephalogram signal of a user in a noninvasive manner; a feature extraction module, config- (Continued)

ured to: perform dimension reduction processing on a combined feature set composed of an electrocardiogram feature and an electroencephalogram feature to obtain a plurality of dimension-reduced combined feature sets, and select an electrocardiogram feature and an electroencephalogram feature meeting a preset criteria of correlation by analyzing a correlation between the plurality of dimension-reduced combined feature sets and a blood glucose concentration value to constitute an optimized combined feature set; and a multimodal fusion module, configured to input the optimized combined feature set into a plurality of trained neural network models, to obtain a detection result by fusing results of the plurality of neural networks.

5 Claims, 2 Drawing Sheets

(51) Int. Cl.
| | |
|---|---|
| *A61B 5/374* | (2021.01) |
| *G16H 50/20* | (2018.01) |
| *G16H 50/70* | (2018.01) |

(52) U.S. Cl.
CPC .......... *A61B 5/7246* (2013.01); *A61B 5/7264* (2013.01); *G16H 50/20* (2018.01); *G16H 50/70* (2018.01)

(58) Field of Classification Search
CPC ......... A61B 5/374; A61B 5/349; A61B 5/291; A61B 5/28; A61B 5/256; A61B 5/14532; A61B 5/0205; A61B 5/35; A61B 5/352; A61B 5/353; A61B 5/355; A61B 5/357; A61B 5/358; A61B 5/36; A61B 5/361; A61B 5/363; A61B 5/364; A61B 5/366; A61B 5/372; G16H 50/20; G16H 50/70; G16H 50/30
See application file for complete search history.

(56) References Cited

OTHER PUBLICATIONS

G. Thippa Reddy et al., "Analysis of Dimensionality Reduction Techniques on Big Data," in IEEE Access, vol. 8, pp. 54776-54788, 2020, doi: 10.1109/ACCESS.2020.2980942. https://ieeexplore.ieee.org/document/9036908. Viewed on Oct. 7, 2024 (Year: 2020).*

Ramon Brena et al. Choosing the Best Sensor Fusion Method: A Machine-Learning Approach. Sensors (Basel). Apr. 20, 2020;20(8):2350. doi: 10.3390/s20082350. PMID: 32326125; PMCID: PMC7219245. Viewed on Oct. 9, 2024 (Year: 2020).*

Mayo Clinic, Diabetes, https://www.mayoclinic.org/diseases-conditions/diabetes/diagnosis-treatment/drc-20371451, viewed on Oct. 8, 2024 (Year: 2024).*

Swapna G. et al., Diabetes detection using deep learning algorithms, ICT Express, vol. 4, Issue 4, 2018, pp. 243-246, ISSN 2405-9595, https://doi.org/10.1016/j.icte.2018.10.005., viewed on Oct. 11, 2024 (Year: 2018).*

Karlo Abnoosian et al. Prediction of diabetes disease using an ensemble of machine learning multi-classifier models. BMC Bioinformatics 24, 337 (2023). https://doi.org/10.1186/s12859-023-05465-z, viewed on Oct. 7, 2024 (Year: 2023).*

Quan Zou et al. Predicting Diabetes Mellitus With Machine Learning Techniques. Front Genet. Nov. 6, 2018;9:515. doi: 10.3389/fgene.2018.00515. PMID: 30459809; PMCID: PMC6232260., viewed on Oct. 7, 2024 (Year: 2018).*

Osadciw, L., Veeramachaneni, K. (2009). Fusion, Decision-Level. In: Li, S.Z., Jain, A. (eds) Encyclopedia of Biometrics. Springer, Boston, MA. https://doi.org/10.1007/978-0-387-73003-5_160. Viewed on Oct. 9, 2024 provided in shared file with other Encyclopedia Entry (Year: 2009).*

Ross, A. (2009). Fusion, Feature-Level. In: Li, S.Z., Jain, A. (eds) Encyclopedia of Biometrics. Springer, Boston, MA. https://doi.org/10.1007/978-0-387-73003-5_157. Viewed on Oct. 9, 2024 provided in shared file with other Encyclopedia Entry (Year: 2009).*

Amin Haq et al. Intelligent Machine Learning Approach for Effective Recognition of Diabetes in E-Healthcare Using Clinical Data. Sensors 2020, 20, 2649. https://doi.org/10.3390/s20092649. Viewed on Oct. 9, 2024 (Year: 2020).*

Huma Naz et al. Deep learning approach for diabetes prediction using PIMA Indian dataset. J Diabetes Metab Disord. Apr. 14, 2020;19(1):391-403. doi: 10.1007/s40200-020-00520-5. PMID: 32550190; PMCID: PMC7270283. (Year: 2020).*

* cited by examiner

PREDIABETES DETECTION SYSTEM AND METHOD BASED ON COMBINATION OF ELECTROCARDIOGRAM AND ELECTROENCEPHALOGRAM INFORMATION

CROSS REFERENCE TO THE RELATED APPLICATIONS

This application is the national stage entry of International Application No. PCT/CN2020/128559, filed on Nov. 13, 2020, which is based upon and claims priority to Chinese Patent Application No. 202010475003.6, filed on May 29, 2020, the entire contents of which are incorporated herein by reference.

TECHNICAL FIELD

The present disclosure relates to the field of medical & healthcare technologies, and more particularly, to a prediabetes detection system and method based on combination of electrocardiogram and electroencephalogram information.

BACKGROUND

There exists a period named as prediabetes in the process of gradually developing from the healthy population with normal blood glucose levels into the diabetic population. The prediabetes refers to a period of impaired blood glucose regulation functions, including impaired fasting blood glucose and impaired glucose tolerance, but having not yet reached diagnostic criteria for diabetes. According to statistics, about 25% of young people and about 20% of adolescents have the prediabetes. About 10% of prediabetic will progress to diabetes every year if no intervention is made. However, if corresponding measures are adopted to intervene in time in the prediabetes phase by, for example, taking drugs, controlling diets, and strengthening exercise, the risk of developing into the diabetes can be reduced by 30%-75%, and the probability of returning to the normal blood glucose levels can rise up to about 70%. Therefore, detection of the prediabetes has great significance.

Existing methods for determining the prediabetes include: 1) Obtaining a blood glucose concentration by blood sampling on an empty stomach. It may be determined as the prediabetes if a fasting blood glucose value ranges between 5.6 mmol/L and 7.0 mmol/L. 2) Carrying out oral glucose tolerance test. Two hours after taking oral glucose, the blood glucose concentration is obtained by blood sampling, and it is determined as the prediabetes if the blood glucose value ranges between 7.8 mmol/L and 11.1 mmol/L. However, all the existing technical solutions need to collect venous blood or fingertip blood, which may cause greater pain and risk of infection to patients, and detection costs are relatively high.

SUMMARY

An objective of the present disclosure is to overcome the above defects of the existing technologies by providing a prediabetes detection method based on combination of electrocardiogram and electroencephalogram information. According to this method, detection of prediabetes is implemented by carrying out oral glucose tolerance tests, by synchronously obtaining electrocardiogram and electroencephalogram information using a wearable device, and then by extracting related electrocardiogram and electroencephalogram features.

According to a first aspect of the present disclosure, there is provided a prediabetes detection system based on combination of electrocardiogram and electroencephalogram information. The system includes:

a signal obtaining module, configured to synchronously obtain an electrocardiogram (ECG) signal and an electroencephalogram (EEG) signal of a user in a noninvasive manner by utilizing a wearable device;

a feature extraction module, configured to: perform dimension reduction processing on a combined feature set composed of an ECG feature and an EEG feature in various ways to obtain a plurality of dimension-reduced combined feature sets, and select the ECG feature and the EEG feature meeting a preset criteria of correlation by analyzing a correlation between the plurality of dimension-reduced combined feature sets and a blood glucose concentration value to constitute an optimized combined feature set; and a multimodal fusion module, configured to respectively input the optimized combined feature set into a plurality of types of trained neural network models, to obtain a detection result indicating whether the user is a prediabetic by fusing output results of the plurality of types of neural networks.

In one embodiment, the synchronously obtaining an electrocardiogram signal and an electroencephalogram signal of a user includes:

placing six ECG electrodes V1 to V6 configured to monitor the ECG signal onto the user's chest, wherein the ECG electrode V1 is placed in a fourth intercostal space at a right border of a sternum, the ECG electrode V2 is placed in a fourth intercostal space at a left border of the sternum, and the ECG electrode V3 is placed in a midpoint of a connecting line between the ECG electrode V2 and the ECG electrode V4, the ECG electrode V4 is placed at an intersection between a left mid-clavicular line and a fifth intercostal space, the ECG electrode V5 is parallel to an anterior axillary line, and the ECG electrode V6 is parallel to a midaxillary line;

wearing an EEG electrode cap on the user's head, six EEG electrodes configured to monitor the EEG signal being provided in the EEG electrode cap, wherein the six EEG electrodes are respectively corresponding to a frontal lobe, an occipital lobe and a parietal lobe of the left hemisphere of a brain, and a frontal lobe, an occipital lobe and a parietal lobe of the right hemisphere of the brain; and carrying out a glucose tolerance test, and starting an ECG collection device and an EEG collection device to synchronously obtain an ECG signal and an EEG signal of the user.

In one embodiment, the feature extraction module is configured to:

extract, from the ECG signal, feature information of a plurality of different segments, and respectively extract, from the EEG signal, EEG feature information of different frequency bands corresponding to different positions of a brain, to constitute the combined feature set;

perform dimension reduction processing on the combined feature set based on a principal component analysis to obtain a first combined feature set;

perform dimension reduction processing on the combined feature set based on an independent component analysis to obtain a second combined feature set;

perform dimension reduction processing on the combined feature set based on a lasso regression analysis to obtain a third combined feature set; and analyze the correlation between the blood glucose concentration and the first combined feature set, the second combined feature set, and the third combined feature set respectively, and then screen out the ECG feature and the EEG feature meeting the preset criteria of correlation, to constitute the optimized combined feature set.

In one embodiment, the correlation is analyzed based on a Pearson correlation analysis, and the criteria of correlation is set as correlation k>0.2 and P≤0.05, wherein P represents a probability of performing hypothesis testing on a correlation coefficient.

In one embodiment, the performing dimension reduction processing on the combined feature set based on a principal component analysis includes:

calculating a covariance matrix of a feature point of each feature in the combined feature set; and calculating eigenvectors of the covariance matrix and eigenvalues corresponding to the eigenvectors:

sorting the eigenvectors according to magnitudes of the eigenvalues to form a matrix $u=[u_1, u_2, u_3, \ldots, u_n]$, the corresponding eigenvalues being $\lambda_1, \lambda_2, \lambda_3, \ldots, \lambda_n$ in descending order, and intercepting, from the matrix u, a certain proportion of top-ranked eigenvalues as new feature points of each feature to achieve data dimension reduction.

In one embodiment, the plurality of types of neural network models include at least two types of a support vector machine, a random forest, a convolutional neural network, a long-short term memory network, and a recurrent neural network.

In one embodiment, the multimodal fusion module is configured to fuse the output results of the plurality of types of neural networks based on a voting method to obtain the detection result indicating whether the user is a prediabetic.

According to a second aspect of the present disclosure, there is provided a prediabetes detection method based on combination of electrocardiogram and electroencephalogram information. The method includes following steps of:

synchronously obtaining an ECG signal and an EEG signal of a user in a noninvasive manner by utilizing a wearable device;

performing dimension reduction processing on a combined feature set composed of an ECG feature and an EEG feature in various ways to obtain a plurality of dimension-reduced combined feature sets, and selecting the ECU feature and the EEG feature meeting a preset criteria of correlation by analyzing a correlation between the plurality of dimension-reduced combined feature sets and a blood glucose concentration value to constitute an optimized combined feature set; and respectively inputting the optimized combined feature set into a plurality of types of trained neural network models, to obtain a detection result indicating whether the user is a prediabetic by fusing output results of the plurality of types of neural networks.

Compared with the existing technologies, the prediabetes detection system and method provided by the present disclosure are noninvasive, painless, convenient and comfortable in use, low in cost, and real-time in monitoring, and can be widely used in prediabetes detection of different groups such as children, adolescents, and the elderly.

Other features and advantages of the present disclosure will become apparent from the following detailed description of exemplary embodiments of the present disclosure with reference to accompanying drawings.

BRIEF DESCRIPTION OF THE DRAWINGS

The accompanying drawings herein are incorporated in and constitute a part of this specification, illustrate embodiments of the present disclosure and, together with the specification, serve to explain the principles of the present disclosure.

DETAILED DESCRIPTION

Figure 1:
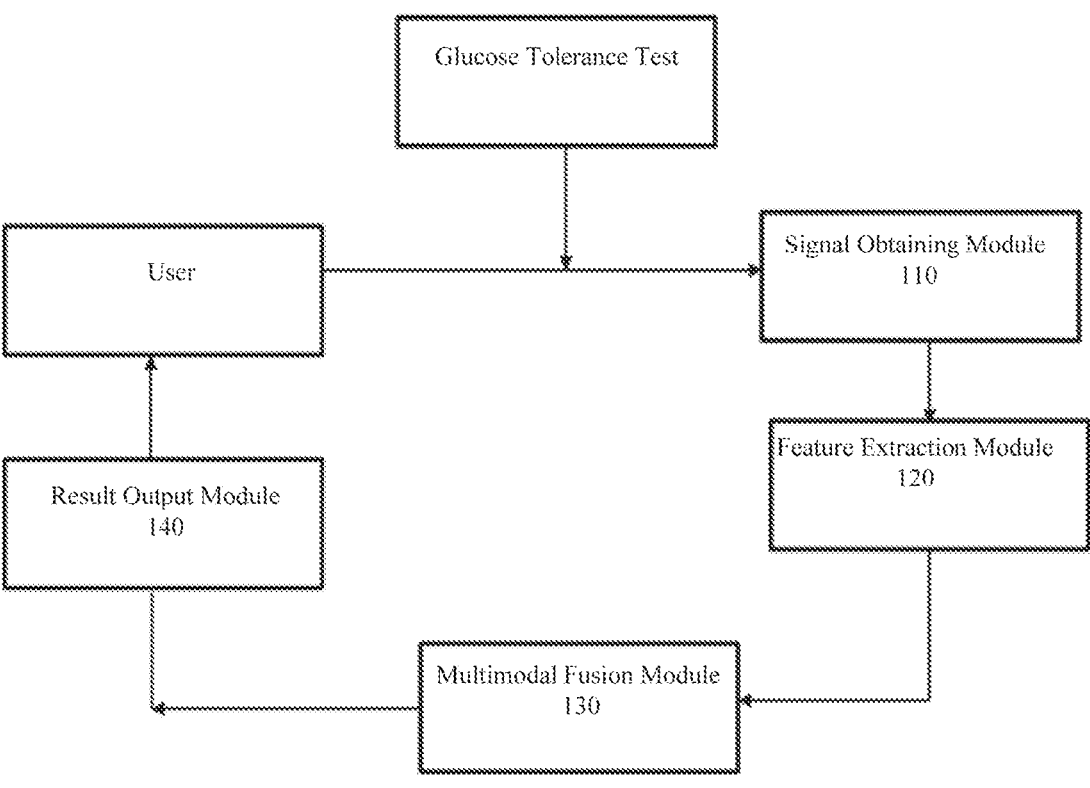
FIG. 1 is a schematic diagram of a prediabetes detection system based on combination of electrocardiogram (ECG) and electroencephalogram (EEG) information according to one embodiment of the present disclosure.

Various exemplary embodiments of the present disclosure will now be described in detail with reference to the accompanying drawings. It is to be noted that the relative arrangement, numerical expressions, and numerical values of the components and steps set forth in these embodiments do not limit the scope of the present disclosure unless otherwise specifically stated.

The following description of at least one exemplary embodiment is actually merely illustrative, and in no way serves as any limitation on the present disclosure and application or use thereof.

Technologies, methods and equipment known to those of ordinary skill in the related art may not be discussed in detail, but where appropriate, the technologies, methods and equipment should be considered as part of the specification.

In all examples shown and discussed herein, any specific values should be interpreted as merely exemplary and not limiting. Therefore, other examples of the exemplary embodiment may have different values.

It is to be noted that similar reference numerals and letters indicate similar items in the following accompanying drawings. Therefore, once an item is defined in one drawing, there is no need to discuss this item further in subsequent drawings.

With reference to FIG. 1, a prediabetes detection system based on combination of electrocardiogram (ECG) and electroencephalogram (EEG) information provided by the embodiments of the present disclosure includes a signal obtaining module 110, a feature extraction module 120, a multimodal fusion module 130, and a result output module 140.

The signal obtaining module 110 is configured to collect an ECG signal and an EEG signal of a user (also referred to as a subject to be tested). For example, the ECG signal and the EEG signal of the user during an oral glucose tolerance test are synchronously obtained by utilizing a wearable device. In one embodiment, steps of synchronously obtaining the ECG signal and the EEG signal are as below. Six ECG electrodes marked as V1 to V6 are placed onto the user's chest. Specifically, the ECG electrode V1 is placed in a fourth intercostal space at a right border of a sternum, the ECG electrode V2 is placed in a fourth intercostal space at a left border of the sternum, the ECG electrode V3 is placed in a midpoint of a connecting line between the ECG electrode V2 and the ECG electrode V4, the ECG electrode V4 is placed at an intersection between a left mid-clavicular line and a fifth intercostal space, the ECG electrode V5 is parallel to an anterior axillary line, and the ECG electrode V6 is parallel to a midaxillary line. Furthermore, a disposable EEG electrode cap is worn on the user's head, and six EEG electrodes configured to monitor EEG information are provided in the EEG electrode cap, wherein the six EEG electrodes are respectively corresponding to a frontal lobe, an occipital lobe and a parietal lobe of the left hemisphere of a brain, and a frontal lobe, an occipital lobe and a parietal lobe of the right hemisphere of the brain. Next, after wearing the ECG electrodes and the EEG electrodes and checking correctly, the user sits still for 10 minutes. After the user breathes smoothly, the oral glucose tolerance test is carried out. For example, the user orally takes 75 grams of glucose. Meanwhile, an ECG collection device and an EEG collection device are started to synchronously obtain ECG signals and EEG signals of the user. After 2 hours, it is stopped collecting the ECG signals and the EEG signals, and ECG and EEG data are exported and saved.

The feature extraction module 120 is configured to perform dimension reduction processing on ECG features and EEG features, and select some ECG features and EEG features which are the most closely related to variations of a blood glucose concentration for subsequent analysis, to improve calculation speed.

The feature extraction module 120 can achieve dimension reduction in a variety of ways, such as using principal component analysis, independent component analysis, lasso regression analysis, and other algorithms. Next, by performing correlation analysis on the dimension-reduced features, some ECG features and EEG features which are the most closely related to variations of the blood glucose concentration are selected.

In one embodiment, a specific implementation process of the feature extraction module 120 includes following steps.

In Step S210, ECG features are extracted from the ECG signals.

Figure 2:
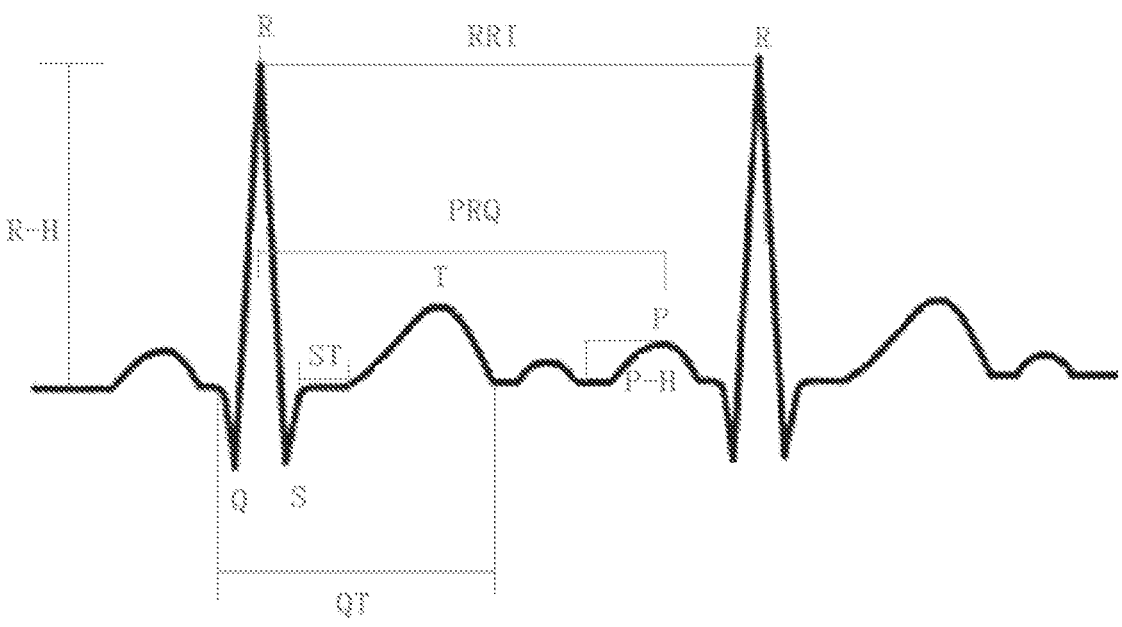
FIG. 2 is a schematic diagram of extracting feature information of different segments from an ECG signal according to one embodiment of the present disclosure.

For example, an ECG signal is analyzed, and feature information of different segments is extracted from the ECG signal, including feature information of 9 different segments RRL RH, PH, QRS, PRQ, QT, QTC, ST, and HR. Labels of feature information of a part of segments are as shown in FIG. 2, and their detailed meanings are as shown in Table 1 below.

TABLE 1

| Feature Information Of Different Segments Extracted From The ECG Signal | |
| --- | --- |
| Title of feature information of different segments of the ECG signal | Meaning |
| RRI | Time span between two adjacent R points in the ECG signal |
| R-H | Height of R wave in the ECG signal |
| P-H | Height of P wave in the ECG signal |
| QRS | Cycle length of QRS wave group |
| PRQ | Time span between R point to P point in the ECG signal |

TABLE 1-continued

| Feature Information Of Different Segments Extracted From The ECG Signal | |
| --- | --- |
| Title of feature information of different segments of the ECG signal | Meaning |
| QT | Time span from beginning of Q wave to end of T wave |
| QTC | QT value calibrated |
| ST | Time distance of straight line segment from S point to T point |
| HR | Beats per minute |

In Step S220, EEG features are extracted from the EEG signals.

Specifically, the EEG signals are analyzed to respectively extract features of signals in different frequency bands of a frontal lobe, an occipital lobe and a parietal lobe of a left hemisphere of a brain, and a frontal lobe, an occipital lobe and a parietal lobe of a right hemisphere of the brain. For example, feature information of 30 EEG signals in total is extracted, as shown in Table 2 below.

TABLE 2

| Feature Information Extracted From The EEG Signals In Different Frequency Bands | |
| --- | --- |
| Title of feature information of the ECG signals | Meaning |
| $F1_T$, $F1_D$, $F1_A$, $F1_B$, and $F1_G$ | Eigenvalues of the frontal lobe of the left hemisphere of the brain in frequency bands of 0-4 Hz, 4-8 Hz, 8-16 Hz, 16-32 Hz, and 32-64 Hz |
| $O1_T$, $O1_D$, $O1_A$, $O1_B$, and $O1_G$ | Eigenvalues of the occipital lobe of the left hemisphere of the brain in frequency bands of 0-4 Hz, 4-8 Hz, 8-16 Hz, 16-32 Hz, and 32-64 Hz |
| $P1_T$, $P1_D$, $P1_A$, $P1_B$, and $P1_G$ | Eigenvalues of the parietal lobe of the left hemisphere of the brain in frequency bands of 0-4 Hz, 4-8 Hz, 8-16 Hz, 16-32 Hz, and 32-64 Hz |
| $F2_T$, $F2_D$, $F2_A$, $F2_B$, and $F2_G$ | Eigenvalues of the frontal lobe of the right hemisphere of the brain in frequency bands of 0-4 Hz, 4-8 Hz, 8-16 Hz, 16-32 Hz, and 32-64 Hz |
| $O2_T$, $O2_D$, $O2_A$, $O2_B$, and $O2_G$ | Eigenvalues of the occipital lobe of the right hemisphere of the brain in frequency bands of 0-4 Hz, 4-8 Hz, 8-16 Hz, 16-32 Hz, and 32-64 Hz |
| $P2_T$, $P2_D$, $P2_A$, $P2_B$, and $P2_G$ | Eigenvalues of the parietal lobe of the right hemisphere of the brain in frequency bands of 0-4 Hz, 4-8 Hz, 8-16 Hz, 16-32 Hz, and 32-64 Hz |

In Step S230, dimension reduction processing is performed on a set of the ECG and EEG features in various ways.

Specifically, considering that dimensions of the ECG feature and the EEG feature extracted are overlong, to achieve fast calculation, dimension reduction processing may be performed on the ECG feature and the EEG feature respectively based on three algorithms, i.e., the principal component analysis, the independent component analysis, and the lasso regression analysis.

In one embodiment, the dimension reduction process based on the principal component analysis is as follows.

Taking a total of 39 features (including 9 ECG features and 30 EEG features) as an example, assuming that each feature has n feature points, a set of all the ECG and EEG features (also referred to as a combined feature set) may be expressed as:

$$X = \{x^{(1)}, x^{(2)}, x^{(3)}, \ldots, x^{(39)}\} \qquad (1)$$

wherein the $i^{th}$ feature may be expressed as:

$$x^{(i)}=(x_1^{(i)},x_2^{(i)},x_3^{(i)}, \ldots ,x_n^{(i)})^T \tag{2}$$

a covariance matrix of the feature set may be expressed as:

$$U = \frac{1}{39}\sum_{i=1}^{39}\left(x^{(i)}\right)\left(x^{(i)}\right)^T \tag{3}$$

wherein the covariance matrix is a square matrix having a size of n×n and n feature points.

Eigenvectors of the covariance matrix and eigenvalues corresponding to the eigenvectors are calculated as below:

$$Uu=\lambda u \tag{4}$$

Further, the eigenvectors are sorted according to magnitudes of the eigenvalues to form a matrix $u=[u_1, u_2, u_3, \ldots , u_n]$, and the corresponding eigenvalues are $\lambda_1, \lambda_2, \lambda_3, \ldots , \lambda_n$ in descending order. In this case, the eigenvector $u_1$ serves as a principal eigenvector (corresponding to the largest eigenvalue), and $u_2$ serves as a secondary eigenvector, and so on. Data dimension reduction is achieved by intercepting, for example, the top 10% values from the matrix u as new feature points of each feature.

In one embodiment, the dimension reduction process based on the independent component analysis is as follows.

It is also assumed that the set of all the ECG and EEG feature may be expressed as:

$$X=\{x^{(1)},x^{(2)},x^{(3)}, \ldots ,x^{(39)}\} \tag{5}$$

wherein the $i^{th}$ feature may be expressed as:

$$x^{(i)}=(x_1^{(i)},x_2^{(i)},x_3^{(i)}, \ldots ,x_n^{(i)})^T \tag{6}$$

Assuming that the feature set dimension-reduced based on the independent component analysis may be expressed as:

$$Q=\{q^{(1)},q^{(2)},q^{(3)}, \ldots ,q^{(39)}\} \tag{7}$$

Based on the independent component analysis, a formula is obtained as below:

$$X=AQ \tag{8}$$

If $W=A^{-1}$, $q^{(i)}=A^{-1}x^{(i)}=Wx^{(i)}$.

$$W = \alpha\left(\begin{bmatrix} 1-2g\left(\omega_1^T x^{(i)}\right) \\ 1-2g\left(\omega_2^T x^{(i)}\right) \\ \ldots \\ 1-2g\left(\omega_n^T x^{(i)}\right) \end{bmatrix}x^{(i)T}\right)$$

(that is, W is expressed in another form), wherein $\alpha$ and g represent proportionality coefficients, whose values are determined using a maximum likelihood method. After the value of the matrix W is determined, the value of the matrix Q can be calculated out, and the value of the matrix Q is the feature set dimension-reduced based on the independent component analysis.

In one embodiment, the dimension reduction process based on the lasso regression analysis is as follows.

It is also assumed that the set of all the ECG and EEG feature may be expressed as:

$$X=\{x^{(1)},x^{(2)},x^{(3)}, \ldots ,x^{(39)}\} \tag{9}$$

wherein the $i^{th}$ feature may be expressed as:

$$x^{(i)}=(x_1^{(i)},x_2^{(i)},x_3^{(i)}, \ldots ,x_n^{(i)})^T \tag{10}$$

Assuming that the feature set dimension-reduced based on the lasso regression analysis may be expressed as:

$$Y=\{y^{(1)},y^{(2)},y^{(3)}, \ldots ,y^{(39)}\} \tag{11}$$

The lasso regression analysis process may be regarded as a convex optimization solution process, i.e., $$J = \frac{1}{39}\left\|y^{(i)} - Kx^{(i)}\right\|^2 \tag{12}$$

wherein J represents a cost function, and K represents a correlation matrix to be solved. By using a Lagrangian function solution method containing a norm, the size of the matrix K may be solved, and an expression of the function J may be obtained.

In Step S240, a correlation analysis is made on the dimension-reduced combined feature set, and some ECG features and EEG features meeting the preset criteria of correlation are selected to form an optimized combined feature set.

Specifically, the dimension-reduced set u of the ECG and EEG features is obtained based on the principal component analysis, the dimension-reduced set Q of the ECG and EEG features is obtained based on the independent component analysis, and the dimension-reduced set Y of the ECG and EEG features is obtained based on the lasso regression analysis. Next, correlations between the blood glucose concentration and the above three dimension-reduced sets of the ECG and EEG features are analyzed respectively based on a Pearson correlation analysis. That is, the correlations between the blood glucose concentration value and the nine ECG features (i.e., RRI, R-H, P-H, QRS, PRQ, QT, QTC, ST, and HR) are analyzed respectively, and the correlations between the blood glucose concentration value and the 30 EEG features (i.e., $F1_T$, $F1_D$, $F1_A$, $F1_B$, $F1_G$, $O1_T$, $O1_D$, $O1_A$, $O1_B$, $O1_G$, and so on) are analyzed respectively. For example, if a correlation coefficient k>0.2 and a value of P (two-tailed)≤0.05 (wherein k is indicative of degree of correlation, P is indicative of probability of hypothesis testing on the correlation coefficient, and P≤0.05 is indicative of a significant correlation), it is considered that there is a higher correlation between the blood glucose value and this feature, and thus this feature is temporarily reserved.

Figure 3:
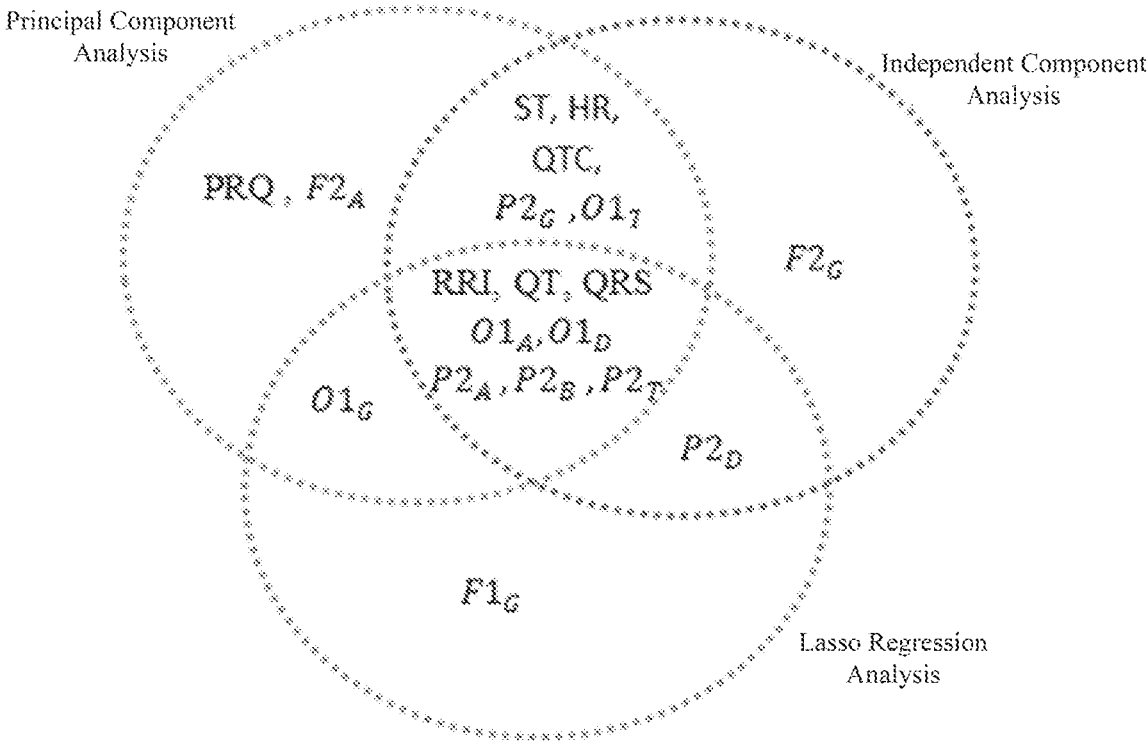
FIG. 3 is a schematic diagram of an ECG feature and an EEG feature selected according to one embodiment of the present disclosure.

After the correlation analysis is completed, ECG and EEG features that satisfy the correlation (k>0.2, and the value of P (two-tailed)≤0.05) in the principal component analysis, the independent component analysis and the lasso regression analysis are selected, and these ECG and EEG features are determined as usable features. As shown in FIG. 3, the finally selected features include three ECG features RRI, QT and QRS, and five EEG features $O1_A$, $O1_D$, $P2_A$, $P2_B$, and $P2_T$.

In the embodiments of the present disclosure, a low-dimension feature set can be obtained by selecting a direction where the feature points have the largest projection variance. The principal component analysis is suitable for a case where samples are in a Gaussian distribution. The independent component analysis does not require the samples to have a Gaussian distribution. The Lasso regression analysis can effectively perform the data dimension reduction and can accurately recognize more important features. By adopting a variety of dimension reduction methods in combination with correlation analysis for feature screening, while effectively performing the data dimension reduction, features that have a strong correlation with the blood glucose concentration can be accurately recognized. In this way, subsequent processing speed can be increased without having a negative effect on the detection accuracy. Furthermore, this method is not sensitive to distribution of feature data, making its scope of application wider.

The multimodal fusion module 130 is configured to obtain a plurality of detection results of prediabetes in different ways based on the set of the ECG and EEG features selected.

Specifically, a support vector machine, a random forest, a convolutional neural network, a long-short term memory network and a recurrent neural network may be employed. The three ECG features RRI, QT and QRS and the five EEG features $O1_A$, $O1_D$, $P2_A$, $P2_B$ and $P2_T$ are extracted as inputs of the above five network models, and appropriate parameters are selected. After iterative training for several times, output results of each of the network model are obtained respectively to indicate whether it belongs to the prediabetes. Further, a fusion result is obtained by using a voting method. For example, if the output results of three or more of the five network models indicate prediabetes, the user is determined as a prediabetic, otherwise the user is not determined as a prediabetic. The detection accuracy can be improved by using the fusion result as the final detection result.

The result output module 140 is configured to display the final determination result to the user. For example, the detection result may be displayed by voice and text, etc.

In summary, in the present disclosure, the ECG signal and the EEG signal are synchronously obtained by using a wearable device to. By performing dimension reduction processing on the ECG features and the EEG features and selecting the optimized combined feature set and by using a prediabetes detection method based on the fusion of a variety of algorithms, a prediabetes detection method, which is noninvasive, painless, convenient, comfortable and low-cost, can be provided for users. This prediabetes detection method can be widely used in the prediabetes detection of different populations such as children, adolescents, and the elderly.

The present disclosure may be a system, a method, and/or a computer program product. The computer program product may include a computer readable storage medium having computer readable program instructions thereon for causing a processor to carry out aspects of the present disclosure.

The computer readable storage medium may be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. More specific examples (a non-exhaustive list) of the computer readable storage medium include: a portable computer diskette, a hard disk, a random access memory (RAW, a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. The computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical fiber transmission, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

The computer program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In a scenario involved with the remote computer, the remote computer may be coupled to the user's computer through any type of network, including a local area network (LAN) or a wide area network (WAN), or may be coupled to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described with reference to flowcharts and/or block diagrams according to the method, apparatus (system) and a computer program product of the embodiments of the present disclosure. It is to be understood that each block of the flowcharts and/or block diagrams, and combinations of blocks in the flowcharts and/or block diagrams, can be implemented by the computer readable program instructions.

These computer readable program instructions may be provided to a processor of a general purpose computer, special purpose computer, or other programmable data processing apparatus to produce a machine, such that these instructions, which execute via the processor of the computer or other programmable data processing apparatus, create means for implementing the functions/acts specified in one or more blocks in the flowcharts and/or block diagrams. These computer readable program instructions may also be stored in a computer readable storage medium that can direct a computer, a programmable data processing apparatus, and/or other devices to function in a particular manner, such that the computer readable medium having instructions stored therein includes an article of manufacture including instructions which implement aspects of the function/act specified in one or more blocks in the flowcharts and/or block diagrams.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in one or more blocks in the flowcharts and/or block diagrams.

The flowcharts and block diagrams in the accompanying drawings illustrate architectures, functions and operations of possible implementations of systems, methods, and computer program products according to a plurality of embodiments of the present disclosure. In this regard, each block in the flowcharts or block diagrams may represent a module, a program segment, or a portion of instructions, which includes one or more executable instructions for implementing the specified logical function(s). In some alternative implementations, the functions denoted by the blocks may occur in a sequence different from the sequences shown in the accompanying drawings. For example, two blocks shown in succession may, in fact, be executed substantially concurrently, or the blocks may sometimes be executed in a reverse sequence, depending upon the functions involved. It is also to be noted that each block in the block diagrams and/or flowcharts and/or a combination of the blocks in the block diagrams and/or flowcharts may be implemented by a special-purpose hardware-based system executing specific functions or acts, or by a combination of a special-purpose hardware and computer instructions. It is well known to those skilled in the art that implementations by means of hardware, implementations by means of software and implementations by means of software in combination with hardware are equivalent.

The descriptions of the various embodiments of the present disclosure have been presented above for purposes of illustration, but are not intended to be exhaustive or limited to the embodiments disclosed. Therefore, it is apparent to an ordinary skilled person in the art that modifications and variations could be made without departing from the scope and spirit of the embodiments. The terminology used herein is chosen to best explain the principles of the embodiments, the practical application or technical improvement over technologies found in the marketplace, or to enable others of ordinary skill in the art to understand the embodiments disclosed herein.

The scope of the present disclosure is limited by the appended claims.

What is claimed is:

1. A non-invasive prediabetes detection method based on combination of electrocardiogram and electroencephalogram information, comprising steps of:

S1, during an oral glucose tolerance test, synchronously obtaining an electrocardiogram (ECG) signal and an electroencephalogram (EEG) signal of a user in a noninvasive manner by utilizing a wearable device;

S2, performing dimension reduction processing on a combined feature set composed of ECG features and EEG features in various ways to obtain a plurality of dimension-reduced combined feature sets, and select the ECG features and the EEG features meeting a preset criteria of correlation by analyzing a correlation between the plurality of dimension-reduced combined feature sets and a blood glucose concentration value to constitute an optimized combined feature set; and S3, respectively inputting the optimized combined feature set into a plurality of trained neural network models, obtaining from each trained neural network model a classification output that classifies the user as prediabetic or non-prediabetic, and determining that the user is prediabetic when a majority of the classification outputs classify the user as prediabetic, and Outputting, via voice or text, a determination indicating whether the user is prediabetic or non-prediabetic;

wherein S1 comprise substeps of:

placing six ECG electrodes V1 to V6 configured to monitor the ECG signal onto the user's chest, wherein the ECG electrode V1 is placed in a fourth intercostal space at a right border of a sternum, the ECG electrode V2 is placed in a fourth intercostal space at a left border of the sternum, and the ECG electrode V3 is placed in a midpoint of a connecting line between the ECG electrode V2 and the ECG electrode V4, the ECG electrode V4 is placed at an intersection between a left mid-clavicular line and a fifth intercostal space, the ECG electrode V5 is parallel to an anterior axillary line, and the ECG electrode V6 is parallel to a midaxillary line;

wearing an EEG electrode cap on the user's head, six EEG electrodes configured to monitor the EEG signal being provided in the EEG electrode cap, wherein the six EEG electrodes are respectively corresponding to a frontal lobe, an occipital lobe and a parietal lobe of a left hemisphere of a brain, and a frontal lobe, an occipital lobe and a parietal lobe of a right hemisphere of the brain; and carrying out the oral glucose tolerance test, and starting an ECG collection device and an EEG collection device to synchronously obtain the ECG signal and the EEG signal of the user:

wherein S2 comprising substeps of:

extracting, from the ECG signal, feature information of a plurality of different segments, and respectively extract, from the EEG signal, EEG feature information of different frequency bands corresponding to different positions of a brain, to constitute the combined feature set;

performing dimension reduction processing on the combined feature set based on a principal component analysis to obtain a first combined feature set;

performing dimension reduction processing on the combined feature set based on an independent component analysis to obtain a second combined feature set;

performing dimension reduction processing on the combined feature set based on a lasso regression analysis to obtain a third combined feature set; and analyzing the correlation between the blood glucose concentration and the first combined feature set, the second combined feature set, and the third combined feature set respectively, and then screen out the ECG features and the EEG features in the first combined feature set, the second combined feature set, and the third combined feature set that meet the preset criteria of correlation, to constitute the optimized combined feature set.

2. The non-invasive prediabetes detection method based on combination of electrocardiogram and electroencephalogram information according to claim 1, wherein the correlation is analyzed based on a Pearson correlation analysis, and the preset criteria of correlation is set as correlation k>0.2 and P≤0.05, P representing a probability of performing hypothesis testing on a correlation coefficient.

3. The non-invasive prediabetes detection method based on combination of electrocardiogram and electroencephalogram information according to claim 1, wherein the performing dimension reduction processing on the combined feature set based on the principal component analysis comprises:

calculating a covariance matrix of a feature point of each feature in the combined feature set; and calculating eigenvectors of the covariance matrix and eigenvalues corresponding to the eigenvectors:

sorting the eigenvectors according to magnitudes of the eigenvalues to form a matrix $u=[u_1, u_2, u_3, \ldots, u_n]$, the corresponding eigenvalues being $\lambda_1, \lambda_2, \lambda_3, \ldots, \lambda_n$ in descending order, and intercepting, from the matrix u, a certain proportion of top-ranked eigenvalues as new feature points of each feature to achieve data dimension reduction.

4. The non-invasive prediabetes detection method based on combination of electrocardiogram and electroencephalogram information according to claim 1, wherein the plurality of types of trained neural network models comprise at least two types of a convolutional neural network, a long-short term memory network, and a recurrent neural network.

5. The non-invasive prediabetes detection method based on combination of electrocardiogram and electroencephalogram information according to claim 1, wherein the determination that the user is prediabetic, further classifies the user as suitable for intervention measures to reduce the risk of progression to diabetes.

* * * * *